US012685705B2

(12) United States Patent
Wang et al.

(10) Patent No.: US 12,685,705 B2
(45) Date of Patent: Jul. 21, 2026

(54) HAIR COLORANT COMPOSITIONS

(71) Applicant: Wella International Operations Switzerland Sarl, Petit-Lancy (CH)

(72) Inventors: Nan Wang, Frankfurt (DE); Ursula Christina Glaser, Wiesbaden (DE); David Sarro, Frankfurt am Main (DE); Giuseppe Esposito, Frankfurt am Main (DE)

(*) Notice: Subject to any disclaimer, the term of this patent is extended or adjusted under 35 U.S.C. 154(b) by 1050 days.

(21) Appl. No.: 17/440,606

(22) PCT Filed: Mar. 18, 2020

(86) PCT No.: PCT/EP2020/057506
§ 371 (c)(1),
(2) Date: Sep. 17, 2021

(87) PCT Pub. No.: WO2020/188001
PCT Pub. Date: Sep. 24, 2020

(65) Prior Publication Data

US 2022/0160614 A1 May 26, 2022

Related U.S. Application Data

(60) Provisional application No. 62/819,933, filed on Mar. 18, 2019, provisional application No. 62/819,917, filed on Mar. 18, 2019.

(51) Int. Cl.

| | |
|---|---|
| ***A61K 8/86*** | (2006.01) |
| ***A61K 8/04*** | (2006.01) |
| ***A61K 8/22*** | (2006.01) |
| ***A61K 8/23*** | (2006.01) |
| ***A61K 8/24*** | (2006.01) |
| ***A61K 8/34*** | (2006.01) |
| ***A61K 8/365*** | (2006.01) |
| ***A61K 8/41*** | (2006.01) |
| ***A61K 8/46*** | (2006.01) |
| ***A61K 8/55*** | (2006.01) |
| ***A61K 8/73*** | (2006.01) |
| ***A61Q 5/08*** | (2006.01) |
| ***A61Q 5/10*** | (2006.01) |

(52) U.S. Cl.
CPC ................ *A61K 8/86* (2013.01); *A61K 8/042* (2013.01); *A61K 8/22* (2013.01); *A61K 8/23* (2013.01); *A61K 8/24* (2013.01); *A61K 8/342* (2013.01); *A61K 8/345* (2013.01); *A61K 8/365* (2013.01); *A61K 8/416* (2013.01); *A61K 8/463* (2013.01); *A61K 8/55* (2013.01); *A61K 8/73* (2013.01); *A61Q 5/08* (2013.01); *A61Q 5/10* (2013.01); *A61K 2800/4324* (2013.01); *A61K 2800/48* (2013.01); *A61K 2800/596* (2013.01); *A61K 2800/882* (2013.01)

(58) Field of Classification Search
CPC ... A61Q 5/08; A61Q 5/10; A61K 8/86; A61K 8/042; A61K 8/22; A61K 8/23; A61K 8/24; A61K 8/342; A61K 8/345; A61K 8/365; A61K 8/416; A61K 8/463; A61K 8/55; A61K 8/73; A61K 2800/4324; A61K 2800/48; A61K 2800/596; A61K 2800/882
See application file for complete search history.

(56) References Cited

U.S. PATENT DOCUMENTS

| | | | | |
|---|---|---|---|---|
| 2015/0053230 A1* | 2/2015 | Myatt | A61K 8/40 132/286 |
| 2017/0165173 A1* | 6/2017 | Flohr | A61K 8/415 |
| 2018/0360739 A1* | 12/2018 | Lorenz | A61K 8/347 |

FOREIGN PATENT DOCUMENTS

| | | | |
|---|---|---|---|
| EP | 2298417 A1 | 3/2011 | |
| EP | 3295924 A1 | 3/2018 | |
| WO | WO-2018053522 A1 * | 3/2018 | A61K 8/02 |

OTHER PUBLICATIONS

International Search Report issued in connection with Application No. PCT/EP2020/057506 dated Jun. 22, 2020.

* cited by examiner

*Primary Examiner* — Marianne C Seidel
*Assistant Examiner* — Amanda Michelle Petritsch
(74) *Attorney, Agent, or Firm* — Dennemeyer & Associates LLC

(57) ABSTRACT

The present invention relates to hair coloring and/or bleaching compositions that can be applied at less aggressive pH environment using relatively low oxidizing agent amounts, as well as their kits and methods thereof. The compositions exhibit low odor and substantially reduced hair fiber damage, are compatible with current dyes and dye precursor systems and result in excellent dye deposition with substantially no lift.

4 Claims, No Drawings

HAIR COLORANT COMPOSITIONS

CROSS-REFERENCE TO RELATED APPLICATIONS

This is a 35 U.S.C. 371 National Stage Patent Application of International Application No. PCT/EP2020/057506, filed Mar. 18, 2020, which claims priority to U.S. provisional application 62/819,933, filed Mar. 18, 2019, and U.S. provisional application 62/819,917, filed Mar. 18, 2019, each of which is hereby incorporated by reference in its entirety.

BACKGROUND

The permanent alteration of the color of keratinous fibers, in particular human hair, by the application of hair dyes is well known. In order to provide the consumer with the hair color and the intensity of color desired, a complex chemical process is sometimes utilized.

Permanent hair dyeing formulations typically comprise oxidative hair dye precursors, which can diffuse into the hair through the cuticle and into the cortex where they can then react with each other and suitable oxidizing agents to form the end dye molecules. Due to the larger size of these resultant molecules they are unable to readily diffuse out of the hair during subsequent washing with water and/or detergents; hence delivering a consumer-desired permanency of color. This reaction typically takes place in an aggressive environment at approximately pH in the presence of an alkalizing agent and in the presence of an oxidizing agent. Moreover, the consumer repeats this process regularly in order to maintain the desired hair color and shade and the intensity of color and to ensure continual, even coverage of the hair including coverage of new hair growth.

Colorant compositions are therefore needed that (i) provide a large range of different resulting colors; (ii) can be applied at less aggressive pH environment; (iii) can be applied using relatively low oxidizing agent amounts; (iv) is easy to manufacture, delivering adequate viscosity; and (v) are shelf life stable.

When a woman grows out her grey hair, she most likely falls into one of two camps. The first is the woman who has a devoted relationship with her colorist, but has doubts about the time, energy and money she puts into covering her grey. The doubt often comes from the fact that when she does color her hair, the grey hair comes in from the roots, inch by inch. The second is the woman who simply accepts the grey hair as it appears on her head, strand by strand. She likely lives her life with a natural, casual contentedness. She probably has realistic expectations about aging and accepts the grey as it comes.

But she may not have very many options to completely embrace the grey by coloring all of her non-grey hair grey for a variety of reasons. She may feel that the gray may not look natural. Or she may not like altering her base grey color, may fear a high commitment to continue coloring her hair because of re-growth lines, and/or may fear that when the grey color fades, it might fade to a color other than her natural gray (e.g., brassy off-tone after color fades).

SUMMARY

It has been surprisingly found that the hair coloring compositions described herein can address these needs not only at lower pHs, but also with very low amounts of oxidizing agent. For example, the hair coloring compositions described herein have a pH of less than 9 and a buffering system that maintains the pH of the compositions between 6 and 8. In addition, the hair coloring compositions described herein comprise less than 2 wt. % of at least one oxidizing agent relative to the total weight of the hair coloring compositions. Moreover the compositions exhibit low odor and substantially reduced hair fiber damage. Finally, the compositions described herein are compatible with current dyes and dye precursor systems and result in excellent dye deposition with substantially no lift.

It has also been surprisingly found that the hair coloring compositions the hair coloring compositions described herein address one or more of the aforementioned fears that women who want to embrace their grey hair color may have. For example, the hair coloring compositions described herein provide resulting grey color that fades within the grey color space, with little to no appearance of brassy off-tone after color fades. Moreover, the compositions exhibit low odor, substantially reduced peroxide concentrations, and substantially reduced hair fiber damage. Finally, the compositions described herein are compatible with current dyes and dye precursor systems and result in excellent dye deposition and improved grey enhancement with substantially no lift and without substantially altering the base gray color.

DESCRIPTION

As used herein the term "hair" to be treated can be "living" i.e. on a living body or can be "non-living" i.e. in a wig, hairpiece or other aggregation of non-living keratinous fibers. Mammalian, preferably human hair is preferred. However wool, fur and other keratin containing fibers are suitable substrates for the compositions according to the present disclosure.

The term "about" as used herein can allow for a degree of variability in a value or range, for example, within 10%, within 5%, or within 1% of a stated value or of a stated limit of a range. Unless specified otherwise herein, the term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more. In some instances, "substantially" means entirely or 100%.

Unless specified otherwise herein, the term "substantially no" as used herein refers to a minority of, or mostly no, as in less than about 10%, 5%, 2%, 1%, 0.5%, 0.01%, 0.001%, or less than about 0.0001% or less.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.10% to 0.5%, 1.10% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

All percentages are by weight of the total composition unless specifically stated otherwise. When more than one composition are used during a treatment, the total weight to be considered is the total weight of all the compositions applied on the hair simultaneously (i.e. the weight found "on head") unless otherwise specified. All ratios are weight ratios unless specifically stated otherwise. All molar concentrations are by volume of the total composition and presented as number of moles of component(s) in one litre of the composition, or "mole/1". When more than one composition are used during a treatment, the total volume to be considered is the total volume of all the compositions applied on the hair simultaneously (i.e. the volume found "on head") unless otherwise specified.

As described herein, this disclosure relates to a hair coloring composition comprising: i) at least one buffering system; ii) less than 2 wt. % of at least one oxidizing agent relative to the total weight of the hair coloring or bleaching composition; and iii) at least one gel network thickener system comprising a) a first surfactant component selected from C14 to 30 alkyl phosphate, C14 to C30 alkyl ether phosphate and a mixtures thereof, b) a second component selected from C14 to C30 fatty alcohols and c) a third surfactant component selected from polyoxyethylene C8 to C30 alkyl ethers; wherein: the composition has a pH of less than 9 and the buffering system maintains the pH of the composition between 6 and 8.

As described herein, this disclosure relates to a hair coloring composition comprising: at least one primary dye and at least one dye coupler, each selected to give hair color in the CIE L*a*b* grey color space and hair color that fades in the CIE L*a*b* grey color space; optionally at least one buffering system; less than 2 wt. % of at least one oxidizing agent relative to the total weight of the hair coloring composition; at least one gel network thickener system; and wherein the hair coloring composition has a pH of less than 9, preferably of about 8 or less, more preferably from about 6 to about 8; and wherein the hair color fades within the CIE L*a*b* grey color space are defined by the following L*a*b* values: $-1<a<4$, $0<b<12$ and $25<L<80$.

Buffering System

According to the present disclosure the compositions can comprise at least one buffering system. The buffering system helps maintain the pH of the compositions described herein at less than 9. In addition, the buffering system can help maintain the pH of the hair coloring compositions described herein between 6 and 8.

The buffering system can be comprised in the at least one of the oxidizing agent and the at least one gel network thickener system. Or the buffering system can be comprised as a component separate to the at least one of the oxidizing agent and the at least one gel network thickener system.

The buffer system can comprise a buffering acidic compound, and a buffering alkali compound. The buffering acidic compound is selected from the group consisting of organic and inorganic acids; e.g., from the group consisting in sulphurous acid, sulphuric acid, hydrochloric acid, hyponitrous acid, nitrous acid, nitric acid, phosphoric acid, phosphorous acid, citric acid, malic acid, and their mixtures; or from the group consisting in phosphoric acid, phosphorous acid, citric acid, malic acid, hydrochloric acid, hyponitrous acid and their mixtures; or the buffering acidic compound is phosphoric acid, hydrochloric acid, hyponitrous acid, and their mixtures; or wherein the buffering acidic compound is phosphoric acid.

The buffering alkali compound is selected from the group consisting of alkali metal salts, amino acids, and salts thereof; or from the group consisting in glycine, alkali metal salts, amino acids, chlorides, nitrates and salts thereof; or alkali metal of chlorides, nitrates and/or phosphoric acid, glycine and salts thereof; alkali metal of phosphoric acid and salts thereof; or disodium phosphate and potassium chloride.

The buffer system can comprise a buffering acidic compound being phosphoric acid, and a corresponding buffering alkali compound being disodium phosphate. Alternatively, the buffer system comprises a buffering acidic compound being phosphoric acid, and a corresponding buffering alkali compound being glycine; or a buffering acidic compound being citric acid, and a corresponding buffering alkali compound being disodium phosphate; or a buffering acidic compound being 5 citric acid, and a corresponding buffering alkali compound being glycine.

The buffering acidic compound and the buffering alkali compound are present in amounts sufficient for providing a buffering effect of reference. The buffering effect of reference is equivalent to a buffer system comprising from 0.10% to 4% phosphoric acid and from 0.10% to 4% disodium phosphate by total weight of the oxidizing agent in a ratio of phosphoric acid to disodium phosphate comprised from 1:1 to 10:1; from 1:1 to 5:1; or from 1:2 to 1:1.

While the buffer system can comprise a buffering acidic compound being phosphoric acid, and a corresponding buffering alkali compound being disodium phosphate, any alternative buffer system may be used, as long as it provides an equivalent buffering effect as the buffer system of reference. The amount alternative buffering acidic compound may be calculated versus the amount of phosphoric acid. The amount of the alternative buffering alkali compound may be calculated versus the amount of disodium phosphate.

Alkalizer

The hair coloring compositions described herein can comprise at least one alkalizer, which can function to adjust the pH of the hair coloring compositions described herein to a desired pH. The alkalizer comprises a source of hydroxide ions. In some instances, the alkalizer comprises about 0.25 mole/L of a source of hydroxide ions. Any source of these ions can be utilized. In particular, sources of sodium, potassium, lithium, calcium, magnesium, barium, ammonium hydroxides and salts, and mixtures thereof, can be used.

It should also be understood that when the composition described herein is used as a hair coloring kit comprising individually packaged components, the concentration of the source of the said ions can be increased in any given component proportionally to the mixing ratio of components in order to achieve the concentration of at least about 0.25 mole/L upon mixing of the components to provide the composition applied to the hair.

pH of Composition

As mentioned herein, the compositions of the present disclosure have a pH of less than 9, from about 8 to about 6.

The pH of the compositions can be determined by using either a Mettler Toledo MP220 or a MP225 pH equipment, fitted with a standard laboratory pH electrode. The equipment is calibrated before each use using standard calibration buffers and using standard calibration procedure.

Oxidizing Agent

The compositions according to the present disclosure can comprise or are used in combination with a composition that comprises at least one source of an oxidizing agent, which can function principally to accelerate the oxidation of the at least one primary dye precursor described herein such that it can react with the at least one dye coupler. For example, the oxidizing agent can be included at a concentration that minimizes lift, but is still sufficient to accelerate the oxidation of the at least one primary dye described herein such that it can react with the at least one dye coupler.

Oxidizing agents for use herein include water-soluble peroxygen oxidizing agents. "Water-soluble," as defined herein, means that in standard condition at least 0.1 g, 1 g, or 10 g of the oxidizing agent can be dissolved in 1 liter of deionized water.

Any oxidizing agent known in the art can be utilized in the present disclosure. Water-soluble oxidizing agents include inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts can be incorporated as monohydrates, tetrahydrates etc. Alkyl and aryl peroxides, and or peroxidases can also be used. Mixtures of two or more such oxidizing agents can be used if desired. The oxidizing agents can be provided in aqueous solution or as a powder which is dissolved prior to use. Preferred for use in the compositions according to the present disclosure are hydrogen peroxide, persulphates, and combinations thereof.

According to the present disclosure the compositions comprise less than 2.5 wt. % or less than 2 wt. % of the at least one oxidizing agent relative to the total weight of the hair coloring composition, e.g., from about 0.1% to about 2% by weight, from about 0.5% to about 1.5% by weight, about 0.2% to about 2% by weight, about 0.5% to about 1% by weight or from about 1% to about 1.9% by weight of at least one oxidizing agent relative to the total weight of the hair coloring composition.

Gel Network Thickener

According to the present invention, the hair colouring and bleaching compositions comprise a gel network thickener system. The gel network thickener system of this invention is typically provided in the dye composition and subsequently mixed with the oxidizing composition. The gel network thickener system of this invention is defined as a thickening system comprising a tertiary system. This system comprises a first anionic surfactant component selected from C14 to C30 alkyl phosphates, C14 to C30 alkyl ether phosphates and or mixtures thereof, a second component selected from C14 to C30 fatty alcohols and a third non-ionic surfactant component selected from polyoxyethylene C14 to C30 alkyl ethers.

Those skilled in the art will recognize that gel network thickener systems usually have a complex structure of networked lamellar bi-layers and/or vesicles and sometimes crystals. These systems usually have creamy appearance and feel and are thus particularly desirable.

In particular the gel network system of the present invention allows for easy and efficient mixing of the dye composition with the oxidizing composition containing a source of hydrogen peroxide. Furthermore, the gel network system delivers the desired mixed viscosity level, independent of the developer composition per se and its viscosity prior to mixing. The latter property is of particular benefit for example in professional hair colour applications in hair salons, where enabling the flexibility to utilize a range of different developer compositions and or viscosity is often particularly desirable.

Without being bound by theory, it is believed that gel network thickener system components described in this invention have appropriate geometrical arrangement in the gel network lamellar bi-layers, preventing bi-layers from deswelling and thus resisting viscosity loss. It is further believed that non-ionic surfactant of this invention has more suppressed swelling due to the higher ionic strength in the dye composition, and thus stability is provided by the ionic surfactant, whereas after dilution with the oxidizing composition, the concentration of ions is reduced leading to nonionic surfactant re-swelling to provide the required additional thickening.

The first surfactant component of the gel network thickener system is selected from C14 to C30, preferably C14 to C18 alkyl phosphate, C14 to C30, preferably C14-C18 alkyl ether phosphate and or mixtures thereof. Preferably the alkyl ether phosphates have an average of from 1 to 20 and most preferably from 1 to 10 ethylene oxide units.

According to the present invention, the gel network system of the present invention comprises as a second component a linear or branched C14 to C30 fatty alcohol and or mixtures thereof. Most preferably, the second component is selected from cetyl, stearyl, cetostearyl or behenyl alcohols or mixtures thereof. Typically, the second component may be comprised within the dye composition or the oxidizing composition or both, preferably the second component is comprised in both compositions. The second component assists in the stabilization of the gel network system and also assists in the maintenance of the desired rheology range particularly at the upper value to prevent excessive stickiness.

The third surfactant component of the gel network thickener system is a non-ionic surfactant, selected from polyoxyethylene C14 to C30 alkyl ethers, comprising one or more polyethyleneoxide chains, preferably having at least 50, preferably from about 50 to 200, most preferably from about 100 to 200 ethylene oxide units. Suitable surfactants include steareth-100, steareth-150, steareth-200 and mixtures thereof. The third surfactant component acts as a co emulsifier and stabilizer of the gel network system. Moreover, whilst not being bound by theory the third surfactant assists in the formation of a soft and smooth composition.

More than one surfactant and or component of each of the above specified types of the surfactants and components may be used in the gel network of the present invention.

Radical Scavenger

The first composition and/or the second composition may comprise one or more radical scavengers. The one or more radical scavengers of the first composition and/or the second composition may be present in a sufficient amount to reduce damage to the hair during an oxidative bleaching or coloring process.

The one or more radical scavengers may be a species that can react with a radical species, preferably a carbonate radical to convert the radical species by a series of fast reactions to a less reactive species. The one or more radical scavengers may be advantageously selected such that the one or more radical scavengers are different from an alkalising agent and/or is present in an amount sufficient to reduce the damage to the hair during the coloring/bleaching process.

The one or more radical scavengers of the first composition and/or the second composition may be selected from the group consisting of: benzylamine, glutamic acid, salicylic acid, imidazole, di-tert-butylhydroxytoluene, hydroquinone, catechol, and mixtures thereof.

Hair Dyes

The hair compositions of the present disclosure are preferably hair coloring compositions which comprise oxidative dyeing compositions. Such compositions comprise oxidative hair dye precursors (also known as "primary intermediates", "primary dyes" or "dyes intermediates" such as the at least one primary dye described herein) that will deliver a variety of hair colors to the hair. These small molecules are activated by the oxidizing agent and react with further molecules, or dye couplers, to form a larger colored complex in the hair shaft.

The hair dye precursors can be used alone or in combination with other hair dye precursors, and one or more can be used in combination with one or more couplers. Couplers (also known as "color modifiers" or "secondary intermediates") are generally colorless molecules that can form colors in the presence of activated precursors, and are used with other precursors or couplers to generate specific color effects or to stabilize the color. The choice of precursors and couplers will be determined by the color, shade and intensity of coloration that is desired. The hair dye precursors and couplers can be used herein, singly or in combination, to provide dyes having a variety of shades ranging from ash blonde to black, but in case of the instant disclosure preferably grey.

These compounds are well known in the art, and include aromatic diamines, aminophenols, aromaticdiols and their derivatives (a representative but not exhaustive list of oxidative dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein. These are: 1,7-Dihydroxynaphthalene (1,7-NAPHTHALENEDIOL), 1,3-Diaminobenzene (m-PHENYLENEDIAMINE), 1-Methyl-2,5-diaminobenzene (TOLUENE-2,5-DIAMINE), 1,4-Diaminobenzene (p-PHENYLENEDIAMINE), 2-Methoxymethyl-1,4-Benzenediamine (MBB), 1,3-Dihydroxybenzene (RESORCINOL), 1,3-Dihydroxy-4-chlorobenzene, (4-CHLORORESORCINOL), 1-Hydroxy-2-aminobenzene, (o-AMINOPHENOL), 1-Hydroxy-3-aminobenzene (m-AMINOPHENOL), 1-Hydroxy-4-amino-benzene (p-AMINOPHENOL), 1-Hydroxynaphthalene (1-NAPHTHOL), 1,5-Dihydroxynaphthalene (1,5-NAPHTHALENEDIOL), 2,7-dihydroxynaphthalene (2,7-NAPHTHELENEDIOL) 1-Hydroxy-2,4-diaminobenzene (4-DIAMINOPHENOL), 1,4-Dihydroxybenzene (HYDROQUINONE), 1-Hydroxy-4-methylaminobenzene (p-METHYLAMINOPHENOL), 6-Hydroxybenzo-morpholine (HYDROXYBENZOMORPHOLINE), 1-Methyl-2-hydroxy-4-aminobenzene (4-AMINO-2-HYDROXY-TOLUENE), 3,4-Diaminobenzoic acid (3,4-DIAMINOBENZOIC ACID), 1-Methyl-2-hydroxy-4-(2'-hydroxyethyl)aminobenzene (2-METHYL-5-HYDROXY-ETHYLAMINO-PHENOL), 1,2,4-Trihydroxybenzene (1,2,4-TRIHYDROXYBENZENE), 1-Phenol-3-methylpyrazol-5-on (PHENYLMETHYLPYRAZOLONE), 1-(2'-Hydroxyethyloxy)-2,4-diaminobenzene (2,4-DIAMINOPHENOXY-ETHANOL HCL), 1-Hydroxy-3-amino-2,4-dichlorobenzene (3-AMINO-2,4-DICHLORO-PHENOL), 1,3-Dihydroxy-2-methylbenzene (2-METHYLRESORCINOL), 1-Amino-4-bis-(2'-hydroxyethyl)aminobenzene (N,N-BIS(2-HYDROXY-ETHYL)-p-PHENYLENE-DIAMINE), 2,4,5,6-Tetraaminopyrimidine (HC Red 16), 1-Hydroxy-3-methyl-4-aminobenzene (4-AMINO-m-CRESOL), 1-Hydroxy-2-amino-5-methylbenzene (6-AMINO-m-CRESOL), 1,3-Bis-(2,4-Diaminophenoxy)propane (1,3-BIS-(2,4-DIAMINO-PHENOXY)-PROPANE), 1-(2'-Hydroxyethyl)-2,5-diaminobenzene (HYDROXYETHYL-p-PHENYLENE DIAMINE SULPHATE), 1-Methoxy-2-amino-4-(2'-hydroxyethylamino) benzene, (2-AMINO-4-HYDROXYETHYLAMINOANISOLE) 1-Hydroxy-2-methyl-5-amino-6-chlorobenzene (5-AMINO-6-CHLORO-o-CRESOL), 1-Hydroxy-2-amino-6-methylbenzene (6-AMINO-o-CRESOL), 1-(2'-Hydroxyethyl)-amino-3,4-methylenedioxybenzene (HYDROXYETHYL-3,4-METHYLENEDIOXY-ANILINE HCl), 2,6-Dihydroxy-3,4-dimethylpyridine (2,6-DIHYDROXY-3,4-DIMETHYLPYRIDINE), 3,5-Diamino-2,6-dimethoxypyridine (2,6-DIMETHOXY-3,4-PYRIDINEDIAMINE), 5,6-Dihydroxyindole (,DIHYDROXY-INDOLE), 4-Amino-2-aminomethylphenol (2-AMINOETHYL-p-AMINO-PHENOL HCl), 2,4-Diamino-5-methylphenetol (2,4-DIAMINO-5-METHYL-PHENETOLE HCl), 2,4-Diamino-5-(2'-hydroxyethyloxy)toluene (2,4-DIAMINO-5-METHYLPHENOXYETHANOL HCl), 5-Amino-4-chloro-2-methylphenol (5-AMINO-4-CHLORO-o-CRESOL), 4-Amino-1-hydroxy-2-(2'-hydroxyethylaminomethyl)benzene HYDROXYETHYLAMINOMETHYL-p-AMINO PHENOL HCl), 4-Amino-1-hydroxy-2-methoxymethylbenzene (2-METHOXYMETHYL-p-AMINOPHENOL HCl), 1,3-Bis(N(2-Hydroxyethyl)N(4-amino-phenyl)amino)-2-propanol (HYDROXYPROPYL-BIS-(N-HYDROXYETHYL-p-PHENYLENEDIAMINE)HCL), 6-Hydorxyindole (6-HYDROXY-INDOLE), 2,3-Indolinedione (ISATIN), 3-Amino-2-methylamino-6-methoxypyridine (HC BLUE NO. 7), 1-Phenyl-3-methyl-5-pyrazolone-2,4-dihydro-5,2-phenyl-3H-pyrazole-3-one, 2-Amino-3-hydroxypyridine (2-AMINO-3-HYDROXYPYRIDINE), 5-Amino-salicylic acid, 1-Methyl-2,6-bis(2-hydroxy-ethylamino)benzene (2,6-HYDROXYETHYLAMINO-TOLUENE), 4-Hydroxy-2,5,6-triaminopyrimidine (2,5,6-TRIAMINO-4-PYRIMIDINOL SULPHATE), 2,2'-[1,2-Ethanediyl-bis-(oxy-2,1-ethanediyloxy)]-bis-benzene-1,4-diamine (PEG-3,2',2'-DI-p-PHENYLENEDIAMINE), 5,6-Dihydroxyindoline (DIHYDROXYINDOLINE), N,N-Dimethyl-3-ureidoaniline (m-DIMETHYL-AMINO-PHENYLUREA), 2,4-Diamino-5-fluortoluenesulfatehydrate (4-FLUORO-6-METHYL-m-PHENYLENEDIAMINE SULPHATE) and 1-Acetoxy-2-methylnaphthalene (1-HYDROXYYETHYL-4,5-DIAMINOPYRAZOLE SULPHATE). These can be used in the molecular form or in the form of peroxide-compatible salts.

In some instances, the at least one primary dye is selected from p-aminophenol, N,N-bis(2-hydroxyethyl)-p-phenylenediamine, 3-methyl-p-aminophenol, methoxymethyl-1,4-diaminobenzene, 2,5-toluenediamine sulfate and mixtures thereof. In addition, the at least one dye coupler is selected from resorcinol, 4-amino-2-hydroxytoluene, 2-methylresorcinol, hydroxyethyl-3,4-methylenedioxyaniline, and mixtures thereof.

The hair coloring compositions of the present disclosure can also include non oxidative hair dyes. i.e. direct dyes which can be used alone or in combination with the above described at least one primary dye and at least one dye coupler. Suitable direct dyes include azo or anthraquinone dyes and nitro derivatives of the benzene series and or melanin precursors and mixtures thereof. Such direct dyes are particularly useful to deliver shade modification or highlights.

The hair dye compositions of the present disclosure will generally comprise from about 0.001% to about 10% of dyes. For example compositions generally comprise from about 0.001% to about 5%, from about 0.10% to about 2% or from about 0.2% to about 1% by weight of dyeing composition of precursors and couplers. Darker shades comprise from 0.001% to about 10% by weight, from about 0.05% to about 7% by weight, or form about 1% to about 5% of precursors and couplers.

Surfactants

The compositions according to the present disclosure can further comprise at least about 0.01% of one or more additional surfactants to those utilized in the gel network thickener system. Surfactants suitable for use herein generally have a lipophilic chain length of from about 8 to about 30 carbon atoms and can be selected from anionic, nonionic, amphoteric and cationic surfactants and mixtures thereof.

Polymers

The composition of the present disclosure can optionally further comprise at least about 0.01% of polymer. The polymer can be chosen, for example, from associative polymers, crosslinked acrylic acid homopolymers, crosslinked copolymers of (meth)acrylic acid and of (C1-C6) alkyl acrylate or polysaccharides. The polymer can also serve as conditioning agents, as described below. The polymer will generally be used at levels of from about 0.01% to about 20.0% by weight of the composition, or of from about 0.1% to about 5%.

Conditioning Agent

The compositions of the present disclosure can comprise or are used in combination with a composition comprising a conditioning agent. Conditioning agents suitable for use herein are selected from silicone materials, amino silicones, fatty alcohols, polymeric resins, polyol carboxylic acid esters, cationic polymers, cationic surfactants, insoluble oils and oil derived materials and mixtures thereof. Additional materials include mineral oils and other oils such as glycerin and sorbitol.

The conditioning agent will generally be used at levels of from about 0.05% to about 20% by weight of the composition, of from about 0.1% to about 15%, of from about 0.2% to about 10%, or from about 0.2% to about 2%.

Particularly useful conditioning materials are cationic polymers and silicones. Conditioners of cationic polymer type can be chosen from those already known by those skilled in the art as improving at least one cosmetic properties of keratin fibers treated with a cosmetic composition. Cationic polymers can be chosen from those comprising units of at least one amine group chosen from primary, secondary, tertiary and quaternary amine groups that can either form part of the main polymer chain or be borne by a side substituent that is directly attached to the main polymer chain.

Silicones can be selected from polyalkylsilioxane oils, linear polydiemthylsiloxane oils containing trimethylsilyl or hydroxydimethylsiloxane endgroups, polymethylphenylsiloxane polydimethylphenylsiloxane or polydimethyldiphenylsiloxane oils, silicone resins, organofunctional siloxanes having in their general structure one or a number of organofunctional group(s), the same or different, attached directly to the siloxane chain. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betain groups. The silicone can either be used as a neat fluid or in the form of an pre-formed emulsion.

Chelants

The composition according to the present invention may further comprise chelants (also known as “chelating agent”, “sequestering agent”, or “sequestrant”) in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and AE Martell & RD Hancock, Metal Complexes in Aqueous Solution, Plenum Press, New York & London (1996), both incorporated herein by reference.

Typically, the composition may comprise a total amount of chelants ranging from at least about 0.01%, alternatively from about 0.01% to about 5%, alternatively from about 0.25% to about 3%, alternatively from about 0.5% to about 1%, by weight of the total composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By “salts thereof”, it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N-N'-diglutaric acid (EDDG), 2-hydroxypropylenediamine-N-N'-disuccinic acid (HPDDS), ethylenediaminetetraacetic acid (EDTA), ethylenedicysteic acid (EDC), ethylenediamine-N-N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, P-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative—$PO_3R_2$, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the composition comprises a chelant selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), Etidronic Acid (HEDP, their salts thereof, their derivatives thereof, and mixtures thereof;

Chelants can be comprised in the at least one of the oxidizing agent and the at least one gel network thickener system. Or chelants can be comprised as a component separate to the at least one of the oxidizing agent and the at least one gel network thickener system. But chelants are usually present with the oxidizing agent, often for stability reasons.

Solvents

Suitable solvents for use in the compositions of the present disclosure include, but are not limited to, water, butoxydiglycol, propylene glycol, alcohol (denat.), ethoxydiglycol, isopropylalcohol, hexylene glycol, benzyl alcohol and dipropylene glycol. Finally, the compositions according to the present disclosure are thus typically provided as an aqueous composition. The compositions of the present disclosure typically comprise from at least about 10%, from about 20%, from about 30% or from about 50% by weight of solvent.

Polysaccharide

The present invention further comprises a polysaccharide. The polysaccharides for use herein are, for example, chosen from glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and nonionic derivatives thereof (hydroxypropyl guar) and bio-polysaccharides, such as xanthan gums, gellan gums, welan gums, scleroglucans, succinoglycans and mixtures thereof. For example, suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328,1980, and in "Industrial Gums-Polysaccharides and their Derivatives", edited by Roy L. Whistler, Second Edition, published by Academic Press Inc.

The polysaccharide is preferably a bio-polysaccharide, particularly preferable are bio-polysaccharides selected from xanthan gum, gellan gum, welan gum, scleroglucan or succinoglycan, for example the material sold under the name Keltrol® T by the company Kelco and the material sold by the name Rheozan® by the company Rhodia Chimie and mixtures thereof. Most preferred are xanthan gum and succinogylcan and mixtures thereof, most preferably xanthan gum. The composition according to the present invention comprises at least about 0.05% of said polysaccharide, preferably from about 0.05% to 0.125% of said polysaccharide by weight of the composition.

Whilst not being bound by theory it is believed that the polysaccharide acts as a plasticiser and tackiness enhancer, and in particular at the above levels it assists in improving root adhesion.

Viscosity

According to the present invention the compositions have a viscosity of from 9 to 16 Pas, preferably from 9 to 15 Pas more preferably from 10 to 14 Pas and most preferably from 11 to 13Pas. A different application have a viscosity of from 1 to 6 Pas, preferably from 2.5 to 4 Pas. Viscosity is determined according to the test method defined hereinafter. This viscosity ranges allow the hair salon professionals to have maximum flexibly to utilize one of numerous application techniques that may be required by any particular client providing a composition which has conditioner like properties and which is not too thick and sticky.

Additional Components

The compositions of the present disclosure can further comprise additional ingredients which include, but are not limited to, additional thickeners and/or rheology modifiers, solvents, enzymes, additional surfactants, conditioning agents, carriers, antioxidants, stabilizers, chelants, perming actives, perfume, reducing agents (thiolactic acid), hair swelling agents and/or polymers. Some of these additional components are detailed hereafter.

In some instances, the compositions of the present disclosure can further comprise up to about 10 wt. % charcoal, such as from about 1 wt. % to about 5 wt. %, about 3 wt. % to about 9 wt. % or about 0.1 wt. % to about 5 wt. % charcoal, such as activated charcoal.

In some instances, the compositions of the present disclosure can further comprise at least one agent that confers a benefit beyond color. For example, the at least one agent that confers a benefit beyond color can make the hair more manageable. An example of such an agent is at least one conditioning agent. Examples of conditioning agents include silicone materials, amino silicones, fatty alcohols, polymeric resins, polyol carboxylic acid esters, cationic polymers, cationic surfactants, insoluble oils and oil derived materials and mixtures thereof. Specific examples of oils include mineral oils, glycerin and sorbitol, and mixtures thereof.

Method of Use

It is understood that the examples of methods of use and embodiments described herein are for illustrative purposes only and that various modifications or changes in light thereof will be suggested to one skilled in the art without departing from the scope of the present disclosure.

After working the mixture for a few minutes, to among other things ensure uniform application to all of the hair, the compositions described herein are allowed to remain on the hair for an amount sufficient to allow, e.g., the at least one primary dye and at least one dye coupler to react (usually from about 2 to 60 minutes, typically about 30 to 45 minutes). The consumer then rinses his/her hair thoroughly with water and allows it to dry. It is observed that the hair has changed from its original color to the desired color.

When present in the hair coloring compositions described herein, the optional conditioning agent can be provided in a separate, additional container. The hair coloring compositions described herein can be mixed with the optional conditioning agent immediately before use and applied together, or the conditioner container can be applied (after an optional rinse step) as a post-treatment immediately after the coloring compositions described herein.

According to the present disclosure the methods of coloring hair also comprise embodiments whereby the hair coloring composition is applied to the hair and the mixture is worked for a few minutes (to insure uniform application to all of the hair). The composition is then allowed to remain on the hair in order for the color to develop for a time period of less than about 20 minutes, less than about 15 minutes, from about 5 minutes to about 10 minutes, 2 minutes to about 60 minutes, for about 40 minutes or for about 10 minutes. The consumer then rinses his/her hair thoroughly with water and allows it to dry and or styles the hair as usual. Such method provides additional convenience to consumer by permitting faster coloring.

The kits described hereinabove are well known in the art and the composition in each container can be manufactured utilizing any one of the standard approaches, these include a) 'Oil in water' process, b) 'Phase Inversion' process and c) 'One-pot' process. For example, when using "oil in water" process, surfactants of the present disclosure are added to approximately 50% of total water amount of the composition at about 90° C., homogenized for 15 to 30 min, then cooled to room temperature thus forming gel network thickener premix; this premix is then mixed cold with remaining amounts of water, other optional components and oxidizing agent or a source of hydroxide ions, thus forming first or second part of the above described coloring kit.

The present disclosure can be utilized in a variety of packaging and dispensing devices. These dispensing devices can come in the form of separate devices which can be used independently or in combination with one another. Typically, the hair coloring compositions are contained within separate single or multi compartment containers so that the compositions can be stored separately from one another before use. The compositions are then mixed together by a mixing means and then applied to the consumer's hair by an application means. Thus, for example, in the hair coloring compositions described herein, component corresponding to the less than 2 wt. % of at least one oxidizing agent relative to the total weight of the composition (the oxidizing agent is sometimes referred to as "the developer") is contained in a container separate from the other components, such as the buffering system, the gel network thickener system, the primary dye (if present) and the at least one coupler (if present), etc. Both set of components are mixed together prior to use. It is disclosed a kit, comprising a first part comprising at least one oxidizing agent and a second part comprising the other components, for obtaining a hair coloring or bleaching composition as defined herewith or for obtaining a hair coloring composition as defined herewith.

One common packaging device that can be used for the present disclosure involves storing the developer in a container such as a bottle, tube, aerosol, or a sachet and separately storing a dye composition in an additional compartment within the developer container or in a separate container which can be identical such as a dual sachet or aesrosol systems for example or different such as a bottle and tube system. In some instances, the hair coloring compositions described herein can further comprise a pigment that is indicative of the final color that will develop from the hair coloring composition. The pigment need not itself impart the color on the hair. A dye or a dye system can be present, which, e.g., upon reaction with the developer, will produce the final color that will develop from the hair coloring compositions described herein.

The consumer can mix a developer composition and a dye composition comprising at least one primary dye and at least one dye coupler, by any means. This can simply involve the use of a mixing bowl into which the lotions are dispensed and then mixed, e.g., using a mixing means such as a tool. Alternatively, it can involve the addition of one of the compositions into the container of the other composition, (typically the dye lotion is added to the developer lotion), followed by manual shaking or mixing with a tool. Another system involves the perforation or displacement of a seal located between the separate compartments of the dye and developer compositions within a single container or sachet followed by manual mixing within the container or in a separate and or additional container.

An example of such devices is the so called 'twist and go' devices. These devices allow the consumer to twist the base of a container holding the at least one primary dye and at least one dye coupler (e.g. in separate or same containers) which enables a communication port to open that exposes the base of the bottle holding the at least one primary dye and at least one dye coupler and the top of the bottle holding the developer. The two components are mixed and the consumer dispenses the product by squeezing the flexible top portion of the bottle for dispensing.

Alternatively, more complex devices can be utilized, whereby the developer, at least one primary dye, and at least one dye coupler are mixed upon actuation of dispensing. An example of such as a complex system is a dual aerosol system e.g. bag-in-can or piston. The at least one primary dye, at least one dye coupler, and developer are stored separately in two aerosol cans within one device, a propellant being used to pressurize the contents of the can or bag in can or piston and a valve providing the control of dispensation. When the consumer actuates the valve, the at least one primary dye, at least one dye coupler, and developer are dispensed simultaneously out of the cans and are mixed together via a static mixer just before dispensing the product onto the hair. The ratio of the at least one primary dye, at least one dye coupler, and developer can be manipulated by the viscosity of the products, the can pressure, or by altering the flow channel sizes through the valve. Additionally, the product can be foamed and delivered via a mousse form.

Another example of such a complex system utilizes a dual piston screw system. The at least one primary dye, at least one dye coupler, and the developer are kept in separate piston cylinder systems within the system and when the consumer actuates a button, two screws are rotated such that the dual pistons inside pressurize the liquid in the cylinders and thus force the products to move through a mixing station and out of the nozzle for dispensing. The ratios of the at least one primary dye, at least one dye coupler, and the developer can be manipulated by the diameter of the cylinder of the package. Additionally, an in line static mixer can be used to aid mixing and such a system can be completely disposable or completely refillable. Yet another system utilizes one or more manually actuated pumps. The product can be premixed in a collapsible sachet. When the consumer actuates the pump, the liquid inside the pump is dispensed. As the manually actuated pump returns to the upright position it forces product from a collapsible sachet. Alternatively, a dual system can be installed whereby two sachets and two pumps are used to deliver the at least one primary dye, at least one dye coupler and the developer lotions to the hair. Alternatively, a single pump connected to two sachets can deliver the product by incorporating the mixing point within the pump. Another embodiment uses a rigid bottle and a dip tube to connect the product to the pump system. Finally, a delaminating bottle can be used in combination with a manually actuated pump where the inner layer of the bottle separates from the outer layer of the bottle which forces the contents of the bottle to be emptied.

Typically, these complex systems offer the advantage of product application independently of the orientation of the product.

The devices described herein above can also be used in combination with a product delivery and or application tool to aid application of the product onto the hair. Again, these devices can be of a very simple nature such as a nozzle attached to one of the containers or a separate applicator device such as a comb or brush. Such combs and brushes can be adapted in order to achieve particular effects, whether it be quick and even coverage or root/hairline touch up, or highlights or streaks. Alternatively, the container or one of the containers can be provided with a comb attached to or instead of the dispensing nozzle whereby the product is dispensed through hollow tines and dispensing apertures located in the comb tines. The comb tines can be provided with single or multiple openings along the tines to improve product application and evenness especially root to tip. Product dispensation can be achieved by mechanical pressure applied to the container for example delaminating bottles or any of the mechanisms described hereinabove. The comb can be provided on the container such as to facilitate easy application and can be positioned vertically (so called verticomb) or at an angle to allow the consumer to access all areas. All devices can be designed to have inter-changeability, so that a range of different tools for hair application can be provided to the consumer.

Additional device technology can be used to assist in the penetration of the product into the hair. Examples of such technology include heating devices, ultraviolet light devices and ultrasound devices.

Viscosity Test Method

Viscosity measurements are carried out on a controlled stress rheometer of AR500, AR1000 or AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The final hair colouring mixture is prepared for example by mixing the required parts of the composition in a professional hair stylist's mixing bowl with the professional hair stylist's brush to ensure the even mixed consistency (standard mixing time 1 minute). The product is loaded into the geometry as per standard procedure and the measurement commences at 5 min after the mixture preparation. Shear stress value at 10 sec-1 shear rate is obtained from the shear stress vs. shear rate curve, and the corresponding viscosity is calculated by dividing the obtained shear stress by 10.

Further embodiments of certain components of the disclosure are described below.

The permanent alteration of the hair color by the application of hair dyes is well known. In order to provide the consumer with the shade and the intensity of color desired, a complex chemical process is utilized. Permanent hair dyeing formulations typically comprise oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of color. This reaction typically takes place in an aggressive environment at approximately pH 10 in the presence of an alkalizing agent and an oxidizing agent. Typically an oxidizing composition (also called developer and/or oxidizing component) comprising the oxidizing agent and a dye composition (also called tint or dye component) comprising the alkalizing agent and if present the precursors dye molecules are mixed shortly before use. The consumer repeats this process regularly in order to maintain the desired hair color and shade and the intensity of color and to ensure continual, even coverage of the hair including coverage of new hair growth.

Definitions

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

By "hair coloring" composition it is meant a composition suitable for changing the color of hair. The hair coloring composition is referred hereinafter as "the composition", unless otherwise specified. The hair coloring composition can comprise oxidative dye precursors, direct dyes or even no, or substantially no, dyes in case of bleaching only compositions where the change of color is mainly caused by the degradation of the natural melanin contained in the hair shaft by the oxidizing agent. The term "hair coloring" composition as used herein covers hair bleaching and hair oxidative dyeing products.

All percentages are by weight of the hair coloring composition, i.e. of the ready-to-use composition, unless otherwise specified. When more than one composition are used during a treatment, the total weight to be considered is the total weight of all the compositions applied on the hair simultaneously (i.e. the weight found "on head"), typically resulting from mixing an oxidative composition (also called developer and/or oxidizing composition/component) with a dye composition (also called tint, and/or dye composition/component), unless otherwise specified. All ratios or percentages are weight ratios or weight percentages unless specifically stated otherwise.

Other Ingredients

The composition according to the present invention may comprise, in addition to the ingredients indicated above, further ingredients in order to further enhance the properties of the composition, as long as these are not excluded by the claims.

Suitable further ingredients include, but not limited to: solvents; oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Solvents

The composition according to the present invention may further comprise a solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polyglycerol); propylene carbonate; and mixtures thereof.

In one embodiment, the solvent may be selected from the group consisting of water, ethanol, propanol, isopropanol, glycerol, 1,2-propylene glycol, hexylene glycol, ethoxy diglycol, and mixtures thereof.

Typically, the composition may comprise water as a main ingredient, particularly in a total amount ranging from at least about 50%, alternatively from at least about 60%, alternatively from at least about 70%, by weight of the total composition. Typically, when present, the composition comprises a total amount of organic solvents ranging from about 1% to about 30%, by weight of the total composition.

Oxidizing Agents

The composition according to the present invention may further comprise at least one source of an oxidizing agent. Any oxidizing agent known in the art may be used. Preferred oxidizing agents are water-soluble peroxygen oxidizing agents. As used herein, "water-soluble" means that in standard conditions at least about 0.1 g, preferably about 1 g, more preferably about 10 g of the oxidizing agent can be dissolved in 1 liter of deionized water at 25° C. The oxidizing agents are valuable for the initial solubilisation and decolorisation of the melanin (bleaching) and accelerate the oxidation of the oxidative dye precursors (oxidative dyeing) in the hair shaft. In short, it is possible to completely remove color by using reducing or bleaching agents. Typically, the composition may comprise a total amount of oxidizing agents ranging from about 0.1% to about 10%, alternatively from about 1% to about 7%, alternatively from about 2% to about 5%, by weight of the total composition.

Suitable water-soluble oxidizing agents include, but are not limited to: inorganic peroxygen materials capable of yielding hydrogen peroxide in an aqueous solution.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use.

In a specific embodiment, the composition comprises a water-soluble oxidizing agent selected from the group consisting of hydrogen peroxide, percarbonates (which may be used to provide a source of both oxidizing agent and carbonate ions and or ammonium ions), persulphates, and mixtures thereof.

When the composition of the present invention is obtained by mixing a developer composition and a tint composition prior to use, the oxidizing agent may be present in the developer composition. The developer composition may be based on any desired formulation chassis, including any commercial product, for example an oil-in-water emulsion. Typical developer compositions comprise about 6% or about 9% of the H2O2 relative to the total weight of the developer composition. A commercial example is the Welloxon® Emulsion with respectively about 6% and about 9% H2O2, marketed by Wella and comprising as INCI ingredients: Water, H2O2, Cetearyl Alcohol, Ceteareth-25, Salicylic Acid, Phosphoric Acid, Disodium Phosphate, Etidronic Acid.

Alkalizing Agents

The composition according to the present invention may further comprise an alkalizing agent. Any alkalizing agent known in the art may be used.

Typically, the composition may comprise a total amount of alkalizing agents ranging from about 0.1% to about 10%, alternatively from about 0.5% to about 6%, alternatively from about 1% to about 4%, by weight of the total composition.

Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine. Preferably, if present, the ammonium ions and carbonate ions are present in the composition at a weight ratio of from 3:1 to 1:10, alternatively from 2:1 to 1:5.

When the composition of the present invention is obtained by mixing a developer and a tint composition prior to use, the alkalizing agent is generally present in the tint composition.

Oxidative Dye Precursors

The composition according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the composition may comprise a total amount of oxidative dye precursors ranging up to about 12%, alternatively from about 0.1% to about 10%, alternatively from about 0.3% to about 8%, alternatively from about 0.5% to about 6%, by weight of the total composition. Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-TH-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the composition of the invention is obtained by mixing a tint composition and a developer composition, the primary intermediates and couplers are usually incorporated into the tint composition.

Direct Dyes

The composition according to the present invention may further comprise compatible direct dyes, in an amount sufficient to provide additional coloring, particularly with regard to intensity. Typically, the composition may comprise a total amount of direct dyes ranging from about 0.05% to about 4%, by weight of the total composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the composition is obtained by mixing a tint composition and a developer composition, the direct dyes are usually incorporated into the tint composition.

Chelants

The composition according to the present invention may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and AE Martell & RD Hancock, Metal Complexes in Aqueous Solution, Plenum Press, New York & London (1996), both incorporated herein by reference.

Typically, the composition may comprise a total amount of chelants ranging from at least about 0.01%, alternatively from about 0.01% to about 5%, alternatively from about 0.25% to about 3%, alternatively from about 0.5% to about 1%, by weight of the total composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N-N'-diglutaric acid (EDDG), 2-hydroxypropylenediamine-N-N'-disuccinic acid (HPDDS), ethylenediaminetetraacetic acid (EDTA), ethylenedicysteic acid (EDC), ethylenediamine-N-N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, 0-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative—$PO_3R_2$, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the composition comprises a chelant selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the composition of the invention is obtained by mixing a tint composition and a developer composition, the chelants may be incorporated in the tint composition and/or in the developer composition. A chelant is usually present in the developer composition for stability reason.

Radical Scavengers

The composition according to the present invention may further comprise a radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring/bleaching process.

Typically, the composition may comprise a total amount of radical scavengers ranging from about 0.1% to about 10%, alternatively from about 1% by weight to about 7%, by weight of the total composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperidine, ethylamine, 3 amino-1-propanol, and mixtures thereof. As used herein, the term "salts thereof"—in the context of radical scavengers—means particularly potassium salts, sodium salts, ammonium salts, and mixtures thereof.

pH Modifiers and Buffering Agents

The composition according to the present invention may further comprise, in addition to the alkalizing agent discussed above, a pH modifier and/or buffering agent in an amount that is sufficiently effective to adjust the pH of the composition to fall within a range from about 3 to about 13, alternatively from about 8 to about 12, alternatively from about 9 to about 11.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The composition according to the invention may further comprise a thickener in an amount sufficient to provide the composition with a viscosity so that it can be readily applied to the hair without unduly dripping off the hair and causing mess.

Typically, the composition may comprise a total amount of thickeners ranging from at least about 0.1%, alternatively at least about 0.5%, alternatively at least about 1%, by weight of the total composition.

Suitable thickeners include, but are not limited to: associative polymers, polysaccharides, non-associative polycarboxylic polymers, and mixtures thereof.

As used herein, the expression “associative polymers” means amphiphilic polymers comprising both hydrophilic units and hydrophobic units, for example, at least one C8 to C30 fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (I) below CH2=C(R1)CH2OB*n*R (I)

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (II) below

CH2=C(R1)COOH (II)

in which R1 is chosen from H, CH3, C2H5 and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (III) below CH2=C(R1)COOB*n*R2 (III)

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical. Anionic amphiphilic polymers may further be cross-linked. The crosslinking agent can be a monomer comprising a group (IV) below

CH2=C< (IV)

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

Preferred associative polymers comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Commercially available materials include those sold as Aculy-22 by Rohm & Haas; Permulen TR1, Carbopol 2020, Carbopol Ultrez-21 by Noveon, Structure 2001/3001 by National Starch. Other preferred associative polymers include polyether polyurethane, commercially available as Aculyn-44/-46 by Rohm and Haas. Further preferred associative polymers include cellulose modified with groups comprising at least one C8-C30 fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid and of C1-C6 alkyl acrylate or (meth)acrylate, and mixtures thereof. Commercially available materials include those sold as Carbopol 980/981/954/2984/5984 by Noveon, Synthalen M/Synthalen L/Synthalen K by 3V Sigma, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and nonionic derivatives thereof (hydroxypropyl guar) and biopolysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328,1980, and in "Industrial Gums-Polysaccharides and their Derivatives", edited by Roy L. Whistler, Second Edition, published by Academic Press Inc., all three being incorporated herein by reference. A preferred polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie. Another preferred polysaccharide is hydroxypropyl starch derivative, particularly hydroxypropyl starch phosphate, commercially available as Structure XL® by National Starch.

Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), N-vinylpyrollidone (Povidone), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth-10 phosphate, Di-cetyl phosphate and Cetearyl alcohol (available as Crodafos CES), and mixtures thereof.

Carbonate Ion Sources

The composition according to the present invention may further comprise a source of carbonate ions, carbamate ions, hydrogen carbonate ions, and mixtures thereof in a sufficient amount to reduce damage to the hair during the coloring process.

Typically, the composition may comprise a total amount of a carbonate ion source ranging from about 0.10% to about 15%, alternatively from about 0.10% to about 10%, alternatively from about 1% to about 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof, alternatively sodium hydrogen carbonate, potassium hydrogen carbonate, and mixtures thereof, alternatively ammonium carbonate, ammonium hydrogen carbonate, and mixtures thereof.

Conditioning Agents

The composition according to the present invention may further comprise a conditioning agent, and/or be used in combination with a composition comprising a conditioning agent.

Typically, the composition may comprise a total amount of conditioning agents ranging from about 0.05% to about 20%, alternatively from about 0.1% to about 15%, alternatively from about 0.2% to about 10%, alternatively from about 0.2% to about 2%, alternatively from about 0.5% to 2%, by weight of the total composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion. Suitable silicones also include: silicones containing groups that may be ionized into cationic groups, for example aminosilicones containing at least 10 repeating siloxane ($Si(CH_3)_2$—O) units within the polymer chain, with either terminal, graft, or a mixture of terminal and graft aminofunctional groups. Example functional groups are not limited to aminoethylaminopropyl, aminoethylaminoisobutly, aminopropyl. In the case of graft polymers, the terminal siloxane units can be $(CH_3)_3Si$—O, $R_{12}(CH_3)_2Si$—O, where $R_{12}$ can be either OH or $OR_{13}$, where $R_{13}$ is a C1-C8 alkyl group, or a mixture of both terminal groups. These silicones are also available as preformed emulsions. Commercially available aminosilicones include those sold as DC-2-8566, DC 7224, DC-2-8220 by Dow Corning; SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones. Suitable aminosilicones may also contain additional functional groups, particularly additional functional groups including polyoxyalkylene, the reaction product of amines and carbinols, and alky chains. Commercially available materials are known as methoxy PEG/PPG-7/3 Aminopropyl Dimethicone (e.g. Abil Soft AF100, by Degussa), or as Bis(C13-15 Alkoxy)PG Amodimethicone (e.g. DC 8500, by Dow Corning). Suitable cationic polymers include, but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about $5\times10^6$, alternatively from about 1000 to about $3\times10^6$. Preferably the cationic polymers are selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinylactams such as vinlypyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); coplolymers of vinyl pyrrolidone and dialkyaminoalkyl acrylates or methactylates, including polymers known as Polquatemium-11 (see Gafquat 440/734/755/755N by ISP; Luviquat PQ11 PM by BASF; Polyquat-11 SL by Sino Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquaternium-53 (e.g. Merquat 2003 by Nalco); copolymers of dimethyaminopropylacrylate (DMAPA), acrylic acid and acrylonitrogens and diethyl sulphate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquatemium-8, Polyquaternium-9, Polyquaternium-12, Polyquaternium-13 Polyquatemium-14, Polyquaternium-15 (e.g. Rohagit KF 720 F by Rohm), Polyquaternium-30 (e.g. Mexomere PX by Chimex), Polyquaternium-33, Polyquaternium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock; Catinal C-100/HC-35/HC-100/HC-200/LC-100/LC-200 by Toho; Celquat SC-240C/SC-230M by National Starch; Dekaquat 400/3000 by Dekker; Leogard GP by Akzo Nobel; RITA Polyquat 400/3000 by RITA; UCARE Polymer JR-125/JR-400/JR-30M/LK/LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C-261N, Cosmedia Guar C-261N by Cognis; DiaGum P 5070 by Freedom Chemical Diamalt; N-Hance Cationic Guar by Hercules/Aqualon; Hi-Care 1000, Jaguar C-17, Jaguar C-2000, Jaguar C-13S, Jaguar C-14S, Jaguar Excel by Rhodia; Kiprogum CW, Kiprogum NGK by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia). 3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epxoypropyl/diethylenetriamine.

5) Cyclopolymers of dialkdiallylamine or of dialkyldiallyammonium, including: Dimethyldially ammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clariant; Mackernium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF; Mackernium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/Super 7 by Ciba); copolymers of dimethyldiallylammoniumchlorides and acrylic acids, including polymers known as polyquaternary-22 (e.g. Merquat 280/Merquat 295 by Nalco).

6) Quaternary diammonium polymers comprising repeat units corresponding to [—N+(R1)(R2)-A1-N+(R3)(R4)-B1-] [2X−], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O-R5-D and —CO—NH-R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X− is an anion derived from inorganic and organic acids. D is chosen from a glycol residue, a bis-secondary diamine residue, a bis-primary diamine residue or a ureylene group. Suitable examples include polymers known as Hexadimethrine chloride, where R1, R2, R3 and R4 are each methyl radicals, A1 is (CH2)3 and B1 is (CH2)6 and X=Cl; as polyquaternium-34 where R1 and R2 are ethyl radicals and R3 and R4 are methyl radicals and A1 is (CH2)3 and B1 is (CH2)3 and X=Br (e.g. Mexomere PAX by Chimax). 7) Polyquaternary ammonium polymers comprising repeating units of formula [—N+(R6)(R7)-(CH2)r-NH-CO-(CH2)q-(CO)t-NH-(CH2)s-N+(R8)(R9)-A-][2X−], in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X− is anion such as a halide. T is an integer chosen to be equal to 0 or 1. A is chosen from divalent radicals such as —CH2-CH2-O-CH2-CH2-. Suitable examples include: polymers known as polyquaternium-2, where r=s=3, q=0, t=0, R6, R7, R8 and R9 are methyl groups, and A is —CH2-CH2-O-CH2-CH2 (e.g. Ethpol PQ-2 from Ethox; Mirapol A-15 by Rhodia); as polyquaternium-17 where r=s=3, q=4, t=1 R6, R7, R8 and R9 are methyl groups, and A is —CH2-CH2-O-CH2-CH2; as Polyquaternium 18, where r=s=3, q=7, t=1 R6, R7, R8 and R9 are methyl groups, and A is —CH2-CH2-O-CH2-CH2; as the block copolymer formed by the reaction of Polyquaternium-2 with Polyquaternium-17, which are known as Polyquaternium 27 (e.g. Mirapol 175 by Rhodia).

8) Copolymers of vinylpyrrolidones and of vinylimidazoles and optionally vinylcaprolactums, including polymers known as Polyquaternary-16 formed from methylvinylimidazolium chlorides and vinylpyrrolidones (e.g. Luviquat FC370//FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquaternary 44 (e.g. Luviquat Care by BASF).

9) Polyamines such as Polyquart H sold by Cognis under the reference name polyethylene glycol (15) tallow polyamine.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen CN/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquaternium 51 (e.g. Lipidure-PMB by NOF), as Polyquaternium 54 (e.g. Qualty-Hy by Mitsui), as Polyquaternium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula (R10-N+(CH3)2)-R11-(Si(CH3)2-0)x-R11-(N+(CH3)2)-R10), where R10 is an alkyl derived from coconut oil, and R11 is (CH2CHOCH2O(CH2)3 and x is a number between 20 and 2000, including polymers known as Quaternium 80

(e.g. Abil Quat 3272/3474 sold by Goldschmidt); silicones containing groups which may be ionised into cationic groups, for example aminosilicones containing at least 10 repeating siloxane —(Si(CH3)2-0) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si-O or R12 (CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si-O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of (R120)(CH3)2Si-O where R12 can be either OH or OR13, where R13 is a C1-C8 alky group, or a mixture of both functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning; SM2059 by GE silicones). Silicones containing groups which may be ionised into cationic groups—for example silicones containing at least 10 repeating siloxane —(Si(CH3)2-O) units within the polymer chain, with either terminal, graft or a mixture of terminal and graft aminofunctional groups, together with additional functional groups. Additional functional groups can include polyoxy alkylene, the reaction product of amines and carbinols, alky chains. For example products known as methoxy PEG/PPG-7/3 Aminopropyl Dimethicone (e.g. Abil Soft AF100 by Degussa). For example products known as Bis (C13-15 Alkoxy) PG Amodimethicone (e.g. DC 8500 by Dow Corning).

In a preferred embodiment, the cationic polymer is selected from the group consisting of polyquaternium 37, polyquaternium 7, polyquaternium 22, polyquaternium 87, and mixtures thereof, particularly from the group consisting of polyquaternium 37, polyquaternium 22, and mixtures thereof.

Surfactants

The composition according to the present invention may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

Typically, the composition may comprise a total amount of surfactants ranging from about 1% to about 60%, alternatively from about 2% to about 30%, alternatively from about 8% to about 25%, alternatively from about 10% to about 20%, by weight of the total composition.

The compositions may comprise a mixture of an anionic surfactant and an amphoteric surfactant with one or more nonionic surfactants. The composition may comprise a total amount of anionic surfactant ranging from about 0.10% to about 20%, alternatively from about 0.1% to about 15%, alternatively from about 5% to about 15%, by weight of the total composition; and a total amount of amphoteric and/or nonionic components, which may range independently from each other from about 0.10% to about 15%, alternatively from about 0.5% to about 10%, alternatively from about 1% to about 8%, by weight of the total composition.

Suitable anionic surfactants include, but are not limited to: salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated (C6-C24) alkyl ether carboxylic acids, polyoxyalkylenated (C6-C24) alkylaryl ether carboxylic acids, polyoxyalkylenated (C6-C24) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Suitable non-ionic surfactants include, but are not limited to: polyethoxylated, polypropoxylated and polyglycerolated fatty acids, alkyl phenols, u-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as $(C_{10}$-$C_{14})$alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of $(C_5$-$C_{20})$alkylbetaines, sulphobetaines, $(C_5$-$C_{20})$alkylamido$(C_1$-$C_6)$alkylbetaines or $(C_5$-$C_{20})$alkylamido$(C_1$-$C_6)$alkylsulphobetaines. Among the amine derivatives, mention may be made of the products sold as Miranol, as described, for example, in U.S. Pat. Nos. 2,528,378 and 2,781,354 and having the structures of: $R_2$—CON $HCH_2CH_2$—$N^+(R_3)(R_4)(CH_2COO^-)$, (VI) in which: R2 is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—$CONHCH_2CH_2$—N(B)(C) (VII) wherein B represents —$CH_2CH_2OX'$, C represents —$(CH_2)_z$—Y', with z=1 or 2, X' is chosen from the —$CH_2CH_2$—COOH group and a hydrogen atom, Y' is chosen from —COOH and —$CH_2$—CHOH—$SO_3H$ radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, $5^{th}$ edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used.

Suitable cationic surfactants include, but are not limited to, the quaternary ammonium salts A) to D) as defined hereinafter:

A) Quaternary Ammonium Salts of General Formula (VIII) Below:

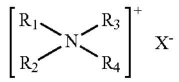

wherein $X^-$ is an anion chosen from halides (chloride, bromide and iodide), $(C_2\text{-}C_6)$alkyl sulphates, such as methyl sulphate, phosphates, alkyl and alkylaryl sulphonates, and anions derived from organic acids, such as acetate and lactate, and wherein $R_1$ to $R_4$ are as below in i) or ii).

i) Radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. $R_4$ is chosen from linear and branched alkyl radicals comprising from 16 to 30 carbon atoms. A suitable cationic surfactant is, for example, a behenyltrimethylammonium salt (for example chloride).

ii) Radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from about 1 to 4 carbon atoms. Radicals $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ may be chosen from $(C_{12}\text{-}C_{22})$alkylamido$(C_2\text{-}C_6)$alkyl and $(C_{12}\text{-}C_{22})$ alkylacetate radicals. A suitable cationic surfactant is, for example, a dicetyldimethyl ammonium salt (for example chloride);

B) Quaternary Ammonium Salts of Imidazolinium of Formula (IX) Below:

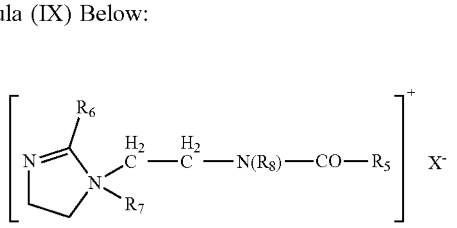

in which $R_5$ is chosen from alkenyl and alkyl radicals comprising from 8 to 30 carbon atoms, for example fatty acid derivatives of tallow, $R_6$ is chosen from a hydrogen atom, $C_1\text{-}C_4$ alkyl radicals and alkenyl and alkyl radicals comprising from 8 to 30 carbon atoms, $R_7$ is chosen from $C_1\text{-}C_4$ alkyl radicals, $R_8$ is chosen from a hydrogen atom and $C_1\text{-}C_4$ alkyl radicals, and $X^-$ is an anion chosen from halides, phosphates, acetates, lactates, alkyl sulphates, alkyl sulphonates and alkylaryl sulphonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary Ammonium Salts of Formula (X):

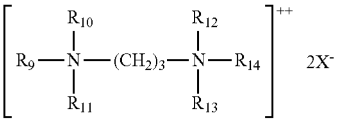

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates nitrates and methyl sulphates. Such diquaternary ammonium salts, for example, include propanetallowdiammonium dichloride.

D) Quaternary Ammonium Salts Comprising at Least One Ester Function, of Formula (XI) Below:

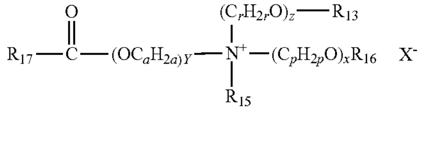

in which: $R_{15}$ is chosen from $C_1\text{-}C_6$ alkyl radicals and $C_1\text{-}C_6$ hydroxyalkyl and dihydroxyalkyl radicals $R_{16}$ is chosen from: a radical $R_{19}C(O)$—, linear and branched, saturated and unsaturated $C_1\text{-}C_{22}$ hydrocarbon-based radicals $R_{20}$, and a hydrogen atom, $R_{18}$ is chosen from: a radical $R_{21}C(O)$—, linear and branched, saturated and unsaturated $C_1\text{-}C_6$ hydrocarbon-based radicals $R_{22}$, and a hydrogen atom, $R_{17}$, $R_{19}$ and $R_{21}$, which may be identical or different, are chosen from linear and branched, saturated and unsaturated $C_7\text{-}C_{21}$ hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X− is an anion chosen from simple and complex, organic and inorganic anions; with the proviso that the sum x+y+z is from 1 to 15, that when x is 0, then R16 is R20 and that when z is 0, then R18 is R22. In one embodiment, the ammonium salts of formula (XI) can be used, in which: R15 is chosen from methyl and ethyl radicals, x and y are equal to 1; z is equal to 0 or 1; n, p and r are equal to 2; R16 is chosen from: a radical R19C(O)-, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)- and a hydrogen atom. Such compounds are commercially available as Dehyquart by Cognis, Stepanquat by Stepan, Noxamium by Ceca, and Rewoquat WE 18 by Rewo-Witco.

Ionic Strength

The composition of the present invention may further have an ionic strength as defined herein of less than about 1.35 mole/kg, alternatively from about 0.10 to about 0.75 mole/kg, alternatively from about 0.20 to about 0.60 mole/kg. Whilst not being bound by theory, it is believed that the ionic strength value may also affect the resultant viscosity and root adhesion properties of the composition. The ionic strength can be affected by salt resources such as the dyes, sodium sulphate, ammonium carbonate anti-oxidants and chelants such as EDDS. The dye tends to have the greatest effect on the ionic strength and thus the amounts added in order to provide any particular shade need to be considered in terms of ionic strength as well as dye outcome in order to prevent viscosity and root adhesion problems.

The ionic strength of the composition is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength. For example the ionic strength of a mixed 0.050 M $Na_2SO_4$ and 0.020 M NaCl solution is: $I=½((2\times(+1)^2\times0.050)+(+1)^2\times0.020+(-2)^2\times0.050+(-1)^2\times0.020)=0.17$ M.

Method of Use/Kits

It is understood that the examples of methods of use and embodiments described herein are for illustrative purposes only and that various modifications or changes in light thereof will be suggested to one skilled in the art without departing from the scope of the present invention. Retail oxidative hair dye compositions are usually sold in kits comprising, in individually packaged components such as separate containers, a dye component (also called "dye cream" for emulsions or "dye liquid" for solutions) comprising the oxidative dye precursors and alkalizing agent which is typically ammonia in a suitable carrier and; a oxidizing component (also called "hydrogen peroxide cream" for emulsions or "hydrogen peroxide liquid" for solutions) comprising the oxidizing agent (usually hydrogen peroxide). The consumer mixes the dye component and oxidizing component together immediately before use and applies it onto the hair. Similarly, retail bleaching compositions are also usually sold as a kit comprising two or three individually packaged components typically in two or three separate containers. The first component comprises the ammonium ion source (e.g. ammonia), the second component comprises the oxidizing agent and the third (optional) component comprises a second oxidizing agent. The bleaching compositions are obtained by mixing the above-mentioned compositions immediately before use.

For, the professional hair salon market, the hair dye component and the oxidizing component and/or bleaching compositions are typically supplied independently to allow the professional to select a preferred combination.

After working the combined mixture for a few minutes (to insure uniform application to all of the hair), the oxidative dye composition is allowed to remain on the hair for an amount sufficient for the dyeing to take place (usually from about 2 to about 60 minutes, typically about 30 to about 45 minutes). The consumer or salon professional then rinses the hair thoroughly with water and/or shampoo and allows it to dry. It will be observed that the hair has changed from its original colour to the desired colour.

In both retail and professional applications, an optional conditioning agent can also be provided. In this embodiment, all three compositions can be mixed immediately before use and applied together, or the conditioning agent can be applied (after an optional rinse step), as a post-treatment immediately after the oxidative dye composition or bleaching composition resulting from the mixture of the other containers.

The kits may also comprise as optional components a pre-treatment composition and/or a colour refresher composition. Such colour refresher compositions comprise at least one pre-formed dye and may be applied to the hair immediately after the oxidative colour i.e. from about 1 minute after oxidative hair dye or bleach application to about 60 days after the application. These colour refresher composition can be used to increase the initial colour obtained and or boost the colour during the wash and style cycle until the next oxidative colouring or bleaching event.

Viscosity

According to the present invention, the dye composition and the oxidizing composition may be, independently from one another, prepared as so called thin liquids or thicker type creams. Typically, thin type liquids have a viscosity of less than about 1000cPs. Thick type creams typically have a viscosity of about XXX cPs.

Upon mixing the dye and oxidizing compositions, the resultant hair coloring and/or bleaching composition preferably have a viscosity of from about 1000 to about 60000cPs, alternatively from about 2000 to about 30000 cPs, alternatively from about 3000 to about 25000 cPs. Viscosity is measured using Brookfield viscometers with cone and plate attachment. For viscosities in the range of about 0 to about 12000 cPs, the Brookfield DV-11 viscometer with S42 plate is used. 2 ml sample of the composition is equilibrated at 26.7° C. for three minutes before the readings are taken at 1 rpm. For viscosities in the range of about 12,000 to about 60,000 cPs, the Brookfield DV-1 viscometer with S52 plate is used. 0.5 ml sample of the composition is equilibrated for 1 minute at 26.7° C. before the readings are taken at 1 rpm. Viscosity values for retail and professional applications, if different, should be provided.

Methods of Manufacture

The kits described hereinabove are well-known in the art and the compositions in each container can be manufactured utilizing any one of the standard approaches, these include a) 'Oil-in-water' process, b) 'Phase Inversion' process and c) 'One-pot' process. For example, when using "oil-in-water" process, surfactants of the present invention are added to approximately 50% of total water amount of the composition at about 90° C., homogenized for 15 to 30 min, then cooled to room temperature thus forming gel network thickener premix; this premix is then mixed cold with remaining amounts of water, other optional components and/or oxidizing agent, thus forming the first and second component parts of the above described bleaching or colouring kit.

Packaging and Dispensing Devices

The present invention may be provided in a variety of packaging devices and/or dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then dispensed from the device and applied to the consumer's hair by an application means.

The most common packaging device which can be used for the present invention involves storing the developer in a container such as a bottle, tube, aerosol, or a sachet and separately storing the dye lotion in an additional compartment within the developer container or more preferably in a separate container which may be identical such as a dual sachet or aerosol systems for example or different such as a bottle and tube system. Any combination may be used and is typically contingent on the type of composition being stored i.e. whether or not it is a thick or thin type. The consumer or hair salon professional may mix the oxidizing component and the dye component by any means. This may simply involve the use of a mixing bowl into which the compositions are dispensed and then mixed, preferably using a mixing means such as a tool. Alternatively, it may involve the addition of one of the compositions into the container of the other composition (typically the dye composition is added to the oxidizing composition), followed by manual shaking or mixing with a tool. Another system involves the perforation or displacement of a seal located between the separate compartments of the dye and oxidizing composition within a single container or sachet followed by manual mixing within the container or in a separate and or additional container.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it may be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps. Highlighting devices comprising a hinged device into which an amount of composition is placed and then used to apply the composition to pre-determined/selected hair strands may also be used.

Additional device technology can be used to assist in the penetration of the product into the hair. Examples of such technology include heating devices, ultraviolet light devices and ultrasound devices.

Foam

Alternatively the compositions of the invention may be provided in the form of foam which is applied to the hair. Foam formation is typically achieved by the use of a foaming agent incorporated within the mixed composition (typically present in either the oxidizing composition or the dye composition or both) in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides (as described herein); polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

Method of Hair Dyeing

The hair coloring composition may be obtained by mixing immediately prior to use a tint composition and a developer composition. A sufficient amount of the mixture is applied to the hair, according to the hair abundance, generally from about 60 to about 250 grams. Upon such preparation the composition is applied to the hair to be dyed and remains in contact with the hair for an amount of time effective to dye the hair. Typically, the hair dye composition is allowed to act on the hair from about 2 to about 60, preferably about 15 to about 45, more preferably about 30 minutes, at a temperature ranging from 15° C. to about 50° C. Thereafter, the hair is rinsed with water to remove the composition and dried. If necessary, the hair is washed with a shampoo and rinsed, e.g., with water or a weakly acidic solution, such as a citric acid or tartaric acid solution, and dried. Optionally, a separate conditioning product may also be provided.

The method of treating hair with the composition may therefore comprise the steps of:

(i) providing a tint composition comprising the gel network thickening system and if present an alkalizing agent and oxidative precursor dyes and/or direct dyes;

(ii) providing a developer composition comprising an oxidizing agent;

(iii) mixing the developer composition with the dye composition to obtain a hair coloring composition according to the invention.

(iv) applying the composition for the oxidative dyeing of keratin fibers onto the hair.

The glycerol can be comprised in the dye composition or the developer composition or distributed in both components. Typically glycerol will be at least comprised in the dye composition to serve as solvent for the dyes.

The method may further comprise waiting a period of time, typically between 2 minutes and 60 minutes, and then rinsing the hair coloring composition from the hair. The hair coloring composition can be applied on hair via applicator bottle or brush. It can be used on full head or partly on single strands (highlight application) as common highlight applicator foils, caps and special applicators can be used, but also freehand techniques such as balayage, with brush and/or combs can be possible. The composition can also be applied as a mousse via a manual spray, a pressurized container or an aerosol mousse. The composition may be dispensed as a solid form to which water is added to generate the oxidant and form a thickened vehicle suitable for hair coloring.

Methods of Making—Kit

The coloring compositions of the invention, and the corresponding tint composition and developer composition, may be manufactured by conventional processes known in the art for manufacturing oxidative dyeing products, and ad-mixing the ingredients of each component composition in suitable vessels, followed by packaging in appropriate individual containers. The components may be for example packaged in plastic or aluminium bottles.

In particular, the present invention may be provided as a kit comprising different components to be mixed by the consumer or salon stylist to obtain a hair dyeing composition according to the invention. Such a kit may comprise a tint composition comprising and a developer composition as indicated above.

The kit may be presented in a single package comprising separate containers for the tint composition, the developer composition, and optionally a conditioner, a color refresher or other hair treatment product, instructions for use, gloves. The instructions for use include the steps of the method described above and optionally provide visual cues or pictures for the desired steps of the method. Kits are usually sold in retail products with enough material in each component for preparing a hair dyeing composition for one use.

The composition may be dispensed as a foam using for example manually-actuable, non-aerosol dispenser such as a pump or squeeze foamers, aerosol mousse. See for example EP 613,728 B1, WO 97/013585 A1, EP 1,716,933A1, U.S. Pat. Nos. 3,709,437, 3,937,364, 4,022,351, 4,147,306, 4,184,615, 4,615,467 and FR 2,604,622. One particular example of a squeeze foamer useful herein is able to dispense from an upright or inverted position such as the one discussed in U.S. Pat. No. 6,604,693 assigned to Taplast, and more specifically, at column 2, line 65, through column 4, line 67 of that patent.

The composition may also be dispensed as a solid form to which water is added to generate the oxidant and form a thickened vehicle suitable for hair coloring.

EXAMPLES

The following examples illustrate oxidative dye compositions according to the present disclosure. It is understood that the examples and embodiments described herein are for illustrative purposes only and that various modifications or changes in light thereof will be suggested to one skilled in the art without departing from the scope of the present disclosure.

Examples 1 and 2

| The following hair coloring compositions are prepared (Part A) Raw Material Name | Sample 1 Wt. % | Sample 2 Wt. % |
|---|---|---|
| Cetearyl Alcohol (and) Dicetyl Phosphate (and) Ceteth-10 Phosphate | 2-12 | 2-12 |
| Cetearyl Alcohol | 0-4 | 0-4 |
| Steareth-200 | 0-4 | 0-4 |
| Propylene Glycol | 1-10 | 1-10 |
| Water Purified, USP, PhEur, JP, JSCI | q.s. | q.s. |
| Sodium Hydroxide | q.s. | q.s. |
| Ammonia (25%) | 4-8 | 0 |
| Ammonium Sulfate | 0-1 | 0 |
| Ascorbic acid | 0.1-1 | 0.1-1 |
| Disodium EDTA | 0.1-1 | 0.1-1 |
| Sodium Sulfate | 0-1 | 0-1 |
| Sodium Sulfite | 0.1-1 | 0.1-1 |
| Disodium Phosphate, anhydrous | 0 | 0.1-5 |
| N,N-BIS(2-HYDROXYETHYL)-P-PHENYLENEDIAMINE SULFATE, monohydrate | 0-2 | 0-2 |
| p-Aminophenol | 0-2 | 0-2 |
| Resorcinol | 0-2 | 0-2 |
| 2-Methylresorcinol | 0-2 | 0-2 |
| HYDROXYETHYL-3,4-METHYLENEDIOXYANILINE HCL | 0-2 | 0-2 |
| 4-Amino-2-Hydroxytoluene | 0-2 | 0-2 |
| Xanthan Gum | 0.1-3 | 0.1-3 |
| PHENOXYETHANOL | 0 | 0.1-1 |
| Perfume | 0.1-1 | 0-1 |
| Trisodium Ethylenediamine Disuccinate | 0.1-5 | 0.1-5 |
| pH | 10.5 | 7.5 |

The pH of the composition of Sample 1 (Pant A) is about 10.5. The pH of the composition of Sample 2 (Part A) is about 7.5.

The following developer composition are prepared (Part B3):

| Developer formula | wt. % |
|---|---|
| Cetearyl Alcohol | 2-6 |
| Ceteareth-25 | 0-2 |
| Sodium Cetearyl Sulfate | 0-1.5 |
| ETIDRONIC ACID (60% in water) | 0.01-0.5 |
| Salicylic acid | 0.01-0.5 |
| Phosphoric acid, solution (85%) | 0.01-1 |
| Disodium Phosphate Anhydrous | 0.01-1 |
| Water Purified | q.s. |

-continued

| Developer formula | wt. % |
|---|---|
| Hydrogene Peroxide | 0.2-2 |
| Paraffinum Liquidum (EU)-(Mineral Oil) | 0-1 |

The pH of the composition of Part B 2.5.

Pant A and Part B are mixed prior to application on hair. The pH of the composition of sample 1 (Part A) mixed with part B is about 10. The pH of the composition of Sample 2 (Part A) mixed with Pant B is about 7.

Examples 3 and 4

The following hair coloring compositions are prepared (Part A):

| Raw Material Name | Sample 1 Wt. % | Sample 2 Wt. % |
|---|---|---|
| CETEARYL ALCOHOL (AND) DICETYL PHOSPHATE (AND) CETETH-10 PHOSPHATE | 9-12% | 9-12% |
| CETEARYL ALCOHOL | 0.1-1% | 0.1-1% |
| Brij S200 | 0.5-2% | 0.5-2% |
| PROPYLENE GLYCOL | 5-10% | 5-10% |
| Water Purified, USP, PhEur, JP, JSCI | 70-80% | 70-80% |
| Sodium Hydroxide (beads) | 0.1-1% | 0.1-1% |
| Ascorbic acid | 0.1-1% | 0.1-1% |
| Disodium EDTA | 0.05-0.5% | 0.05-0.5% |
| Sodium Sulfite | 0.1-1% | 0.1-1% |
| Disodium Phosphate, anhydrous | 0.5-2% | 0.5-2% |
| N,N-BIS(2-HYDROXYETHYL)-P-PHENYLENEDIAMINE SULFATE, monohydrate | 0.5-2% | 0.5-2% |
| p-Aminophenol | 0.005-0.05% | |
| Resorcinol | | 0.005-0.05% |
| 2-Methylresorcinol | 0.1-1% | |
| HYDROXYETHYL-3,4-METHYLENEDIOXYANILINE HCL | 0.1-1% | |
| 4-Amino-2-Hydroxytoluene | | |
| Xanthan Gum | 0.1-1% | 0.1-1% |
| PHENOXYETHANOL | 0.1-1% | 0.1-1% |
| Trisodium Ethylenediamine Disuccinate | 0.1-1% | 0.1-1% |

The viscosity of the composition of Sample 1 (Part A) is below 1000 cPs. The viscosity of the composition of Sample 2 (Part A) is within the range of 1000 to 60000 cPs.

The following developer composition are prepared (Pant B):

| Developer formula | wt. % |
|---|---|
| Cetearyl Alcohol | 2-5% |
| Sodium Cetearyl Sulfate | 0.1-1% |
| ETIDRONIC ACID (60% in water) | 0.005-0.05% |
| Salicylic acid | 0.005-0.05% |
| Phosphoric acid, solution (85%) | 0.005-0.05% |
| Disodium Phosphate Anhydrous | 0.05-0.1% |
| Water Purified | 90-95% |
| Hydrogene Peroxide | 1.5-2.5% |
| Paraffinum Liquidum (EU)-(Mineral Oil) | 0.1-1% |

Part A and Part B are mixed prior to application on hair and the viscosity of the mixed formulations is within the range of 1000 to 60000 cPs (e.g., from 2000 to 30000 cPs or from 3000 to 25000 cPs).

CLAUSES

Clause 1—A hair coloring or bleaching composition comprising:

i) at least one alkalizer;

ii) less than 2 wt. % of at least one oxidizing agent relative to the total weight of the hair coloring or bleaching composition; and iii) at least one gel network thickener system comprising a) a first surfactant component selected from C14 to 30 alkyl phosphate, C14 to C30 alkyl ether phosphate and a mixtures thereof, b) a second component selected from C14 to C30 fatty alcohols and c) a third surfactant component selected from polyoxyethylene C8 to C30 alkyl ethers, wherein said composition further comprises at least 0.05% of a polysaccharide, at least 3% of a polyol selected from propyleneglycol, butoxydiglycol, ethoxydiglycol, hexylene glycol, dipropylene glycol, glycerol, polyglycerol, and mixtures thereof;

wherein the composition has a pH of less than 9 and the buffering system maintains the pH of the composition between 6 and 8.

Clause 2—The composition of clause 1, wherein the component ii) is contained in a container separate from at least one of components i) and iii) and is combined with at least one of components i) and iii) prior to use.

Clause 3—The composition of clause 1, wherein the hair coloring or bleaching composition has a pH of less than 8.

Clause 4—The composition of clause 1, wherein the hair coloring or bleaching composition has a pH of from about 6 to about 8.

Clause 5—The composition of clause 1, wherein the hair coloring or bleaching composition comprises from about 0.2 wt. % to about 2 wt. %, preferably from about 0.5 wt. % to about 1 wt. % of the at least one oxidizing agent.

Clause 6—The composition of clause 1, wherein the hair coloring or bleaching composition further comprises a pigment that is indicative of the final color that will develop from the hair coloring or bleaching composition.

Clause 7—The composition of clause 1, wherein the hair coloring or bleaching composition further comprises up to 10 wt. % charcoal.

Clause 8—The composition of clause 1, wherein the hair coloring or bleaching composition further comprises at least about 0.1 wt. % of at least one chelant.

Clause 9—The composition of clause 8, wherein the chelant is selected from, carboxylic acids (in particular aminocarboxylic acids, such as EDDS (ethylenediaminedisuccinic acid)), phosphonic acids (in particular aminophosphonic acids, such as DTPMP (diethylenetriamine penta (methylene phosphonic acid)) and polyphosphoric acids (in particular linear polyphosphoric acids), their salts and derivatives.

Clause 10—The of clause 1, wherein the composition further comprises at least one agent that confers a benefit beyond color.

Clause 11—The composition of clause 10, wherein the at least one agent makes the hair more manageable.

Clause 12—The composition of clause 10, wherein the at least one agent is at least one conditioning agent.

Clause 13—The composition of clause 12, wherein the conditioning agent is silicone materials, amino silicones, fatty alcohols, polymeric resins, polyol carboxylic acid esters, cationic polymers, cationic surfactants, insoluble oils and oil derived materials and mixtures thereof.

Clause 14—The composition of clause 12, wherein the conditioning agent is mineral oil.

Clause 15—The composition of any preceding claims, wherein the at least one buffering system comprises at least one alkalizer.

Clause 16—The composition of clause 15, wherein the at least one alkalizer comprises a source of hydroxide ions, carbonate ions, carbamate ions, hydrogen carbonate ions or mixtures thereof.

Clause 17—The composition of clause 1, wherein the at least one buffering system comprises at least one of disodium phosphate and/or monosodium phosphate.

Clause 18—A composition according to clause 1 wherein said third surfactant is selected from polyoxyethylene C14 to C30 alkyl ethers having at least 50, preferably from 100 to 200 ethylene oxide units.

Clause 19—The composition of any one of the preceding clauses, wherein the composition has a viscosity of from 9 to 16 Pas, preferably from 9 to 15 Pas more preferably from 10 to 14 Pas and most preferably from 11 to 13Pas.

Clause 20—The composition of any one of the preceding clauses, wherein the composition has a viscosity of from 1 to 6 Pas, preferably from 2.5 to 4 Pas.

Clause 21—The composition of any one of the preceding clauses, wherein the composition comprises at least one oxidative dye precursor or/and at least one pre-formed dye.

Clause 22—A method of treating hair comprising the steps of applying a composition of any one of the preceding clauses, leaving the composition on the hair for from 2 to 60 minutes and subsequently rinsing the composition from the hair.

Clause 23—A hair coloring composition comprising:

i) at least one primary dye and at least one dye coupler, each selected to give hair color in the CIE L*a*b* grey color space and hair color that fades in the CIE L*a*b* grey color space;

ii) optionally at least one buffering system;

iii) less than 2 wt. % of at least one oxidizing agent relative to the total weight of the hair coloring composition; and wherein: the hair coloring composition has a pH of less than 9.

Clause 24—The hair coloring composition of clause 23, wherein the hair color fades within the CIE L*a*b* grey color space defined by the following L*a*b* values: $-1<a<4$; and $0<b<12$.

Clause 25—The hair coloring composition of clause 23, wherein the hair color fades within the CIE L*a*b* grey color space defined by the following L*a*b* value: $25<L<80$.

Clause 26—The hair coloring composition of clause 23, wherein the at least one primary dye is selected from p-aminophenol, N,N-bis(2-hydroxyethyl)-p-phenylenediamine, 3-methyl-p-aminophenol, methoxymethyl-1,4-diaminobenzene, 2,5-toluenediamine sulfate and mixtures thereof.

Clause 26—The hair coloring composition of any one of the preceding clauses 23 to 25, wherein the at least one dye coupler is selected from resorcinol, 4-amino-2-hydroxytoluene, 2-methylresorcinol, hydroxyethyl-3,4-methylenedioxyaniline, and mixtures thereof.

Clause 27—The hair coloring composition of clause 23, wherein the component iii) is contained in a container separate from at least one of components i) and ii) and is combined with at least one of components i) and ii) prior to use.

Clause 28—The hair coloring composition of clause 23, wherein the hair coloring composition has a pH of less than 8.

Clause 29—The hair coloring composition of clause 23, wherein the hair coloring composition has a pH of from about 6 to about 8.

Clause 30—The hair coloring composition of clause 23, wherein the hair coloring composition comprises from about 0.2 wt. % to about 2 wt. % or from about 0.5 wt. % to about 1 wt. % of the at least one oxidizing agent.

Clause 31—The hair coloring composition of clause 23, wherein the hair coloring composition further comprises up to 10 wt. % charcoal.

Clause 32—The hair coloring composition of clause 23, wherein the hair coloring composition further comprises at least about 0.1 wt. % of at least one chelant.

Clause 34—The hair coloring composition of clause 23, wherein the hair coloring composition further comprises at least one agent that confers a benefit beyond color.

Clause 35—The hair coloring composition of clause 34, wherein the at least one agent makes the hair more manageable.

Clause 36—The hair color composition of clause 34, wherein the at least one agent is at least one conditioning agent.

Clause 37—The hair coloring composition of clause 36, wherein the conditioning agent is silicone materials, amino silicones, fatty alcohols, polymeric resins, polyol carboxylic acid esters, cationic polymers, cationic surfactants, insoluble oils and oil derived materials and mixtures thereof.

Clause 38—The hair coloring composition of clause 36, wherein the conditioning agent is mineral oils, glycerin and sorbitol and mixtures thereof.

Clause 39—The hair coloring composition of any preceding clauses 23 to 38, further comprising at least at least one buffering system.

Clause 40—The hair coloring composition of clause 23 wherein the at least one buffering system comprises disodium phosphate.

Clause 41—The hair coloring composition of any one of the preceding clauses 23 to 40, further comprising: iv) at least one gel network thickener system.

Clause 42—The hair coloring composition of any one of the preceding clauses 23 to 41, wherein the composition has a viscosity of from 1000 to 60000 cPs, from 2000 to 30000 cPs or from 3000 to 25000 cPs.

Clause 43—A method of treating hair comprising the steps of applying a composition of any one of the preceding clauses 23 to 42, leaving the composition on the hair for from 2 to 60 minutes and subsequently rinsing the composition from the hair.

The invention claimed is:

1. An aqueous hair coloring composition comprising:

i) at least one primary dye and at least one dye coupler, each selected to give hair color in the CIE L*a*b* grey color space and hair color that fades in the CIE L*a*b* grey color space, and wherein the at least one dye coupler is not resorcinol;

ii) a buffering system comprising phosphoric acid and mono-and/or di-sodium phosphate;

iii) about 0.5 wt. % to about 1.5 wt. % of at least one oxidizing agent relative to the total weight of the hair coloring composition;

iv) at least one gel network thickener system of from 11.6 wt % to about 20 wt % comprising a) a first surfactant component selected from C14 to 30 alkyl phosphate, C14 to C30 alkyl ether phosphate and a mixture thereof, b) a second component selected from C14 to C30 fatty alcohols and c) a third surfactant component selected from polyoxyethylene C14 to C30 alkyl ethers having at least 50 ethylene oxide units;

v) at least 0.05% of a polysaccharide, vi) at least 3% of a polyol selected from propyleneglycol, butoxydiglycol, ethoxydiglycol, hexylene glycol, dipropylene glycol, glycerol, polyglycerol, and mixtures thereof;

vii) an alkalizer comprising a source of hydroxide ions, carbonate ions, hydrogen carbonate ions or mixtures thereof;

viii) a chelant of from about 0.5 wt % to about 1 wt %, comprising an aminocarboxylic acid, an aminophosphonic acid or a mixture thereof, wherein the hair coloring composition has a pH of about 6 to about 8; and buffering system maintains the pH of the composition between 6 and 8, wherein the hair color fades within the CIE L*a*b* grey color space are defined by the following L*a*b* values: $-1<a<4$, $0<b<12$ and $25<L<80$, and wherein the wt %'s are relative to the total weight of the aqueous hair coloring composition.

2. The aqueous hair coloring composition of according to claim 1, further comprising at least one conditioning agent wherein the conditioning agent is one or more of silicone materials, amino silicones, fatty alcohols, polymeric resins, polyol carboxylic acid esters, cationic polymers, cationic surfactants, insoluble oils, oil derived materials, mineral oil and mixtures thereof.

3. A hair coloring composition according to claim 1, wherein the at least one primary dye is selected from p-aminophenol, N,N-bis(2-hydroxyethyl)-p-phenylenediamine, 3-methyl-p-aminophenol, methoxymethyl-1,4-diaminobenzene, 2,5-toluenediamine sulfate and mixtures thereof; and/or wherein the at least one dye coupler is selected from 4-amino-2-hydroxytoluene, 2-methylresorcinol, hydroxyethyl-3,4-methylenedioxyaniline, and mixtures thereof.

4. A kit, comprising a first part comprising at least one oxidizing agent and a second part comprising the other components including the at least one precursor and the at least one coupler, for obtaining the aqueous hair coloring composition according to claim 1.

* * * * *